(12) United States Patent
Atwood et al.

(10) Patent No.: US 6,495,669 B1
(45) Date of Patent: Dec. 17, 2002

(54) FORMATION OF NANOMETER-SCALE STRUCTURES

(75) Inventors: Jerry L. Atwood, Columbia, MO (US); G. William Orr, Northfield, MN (US); Leonard J. Barbour, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/637,221

(22) Filed: Aug. 11, 2000

Related U.S. Application Data

(60) Provisional application No. 60/148,610, filed on Aug. 12, 1999.

(51) Int. Cl.[7] ................................................. C07F 13/00
(52) U.S. Cl. ............................... 534/14; 534/10; 534/15
(58) Field of Search .................................. 534/7, 10–16; 424/1.11, 1.65; 514/290; 568/867

*Primary Examiner*—Dameron L. Jones
(74) *Attorney, Agent, or Firm*—William D. Jackson, Esq.; Locke Liddell & Sapp LLP

(57) ABSTRACT

Amphiphilic, polyhedron-shaped p-sulfonatocalix[4]arene building blocks, which have been shown previously to assemble into bilayers in an antiparallel fashion, assemble in a parallel alignment into spherical and helical tubular structures on the addition of pyridine N-oxide and lanthanide ions. The addition of greater amounts of pyridine N-oxide changed the curvature of the assembling surface and led to the formation of extended tubules. The inventive compositions and methods are useful for drug delivery and construction of nano-devices.

23 Claims, 4 Drawing Sheets

FORMATION OF NANOMETER-SCALE STRUCTURES

CROSS REFERENCE TO RELATED APPLICATIONS

This application claims the benefit of U.S. provisional application Ser. No. 60/148,610 filed Aug. 12, 1999, which is hereby incorporated by reference in its entirety.

STATEMENT REGARDING FEDERALLY SPONSORED RESEARCH & DEVELOPMENT

The U.S. Government has rights in this invention pursuant to Contract No. NSF-9710197 awarded by the National Science Foundation.

BACKGROUND OF THE INVENTION

The present invention generally relates to the preparation of molecular or ionic supramolecular assemblies, and more particularly to the formation of nanometer scale structures, having a substantially enclosed volume.

Encapsulation of one chemical species by another, sometimes termed "host-guest chemistry", is a phenomenon that has a wide range of applicability. For example, encapsulation technology is presently used to produce pressure-sensitive inks for carbon copies and is of interest for use in drug delivery. Encapsulation could play an important role in modifying the physical properties of drug substances to enhance their compounding properties for oral and topical administration. Encapsulation could also be important for development of nano-devices, where it could provide a way of insulating molecular wires from each other much as the myelin sheath functions on neurons. In view of the importance and variety of context in which encapsulation plays a critical role, it would be desirable to control the volume within which a species is encapsulated by another. It would be particularly desirable to have a way in which to control the volume enclosed by an encapsulating species without changing fundamentally the composition, and therefore the chemical reactivity, of that species.

BRIEF SUMMARY OF THE INVENTION

The present invention provides a way of controlling the volume enclosed by encapsulating species and controlling the topology of that enclosed volume. An encapsulating or "clathrating" species that exists either as a spherical cluster or as a tubule is prepared by varying the proportions of the constituents of the encapsulating species.

More specifically, the inventors have found that variation in the proportion of a co-ligand added to a mixture of a calix[4]arene bearing a potential ligating group in the para-position and a n+ metal ion (where n=2–3) changes the topology of the solid-state structure into which the species assembles. Still more specifically, the applicants have found pyridine-N-oxide to be especially useful as a co-ligand when used in conjunction with p-sulfonatocalix[4]arene complexed to lanthanide(III) species.

Accordingly, in carrying out the present invention, there is provided a composition comprising a calixarene, a co-ligand, and a 2+ or 3+ metal ion in a ratio of about 1:1:1 to about 2:8:1. Preferably the calixarene has the structure

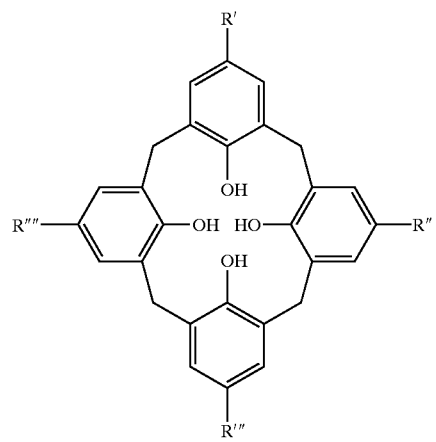

wherein R', R", R''', and R'''' are functional groups capable of binding to a metal ion. More, specifically, R', R", and R''', and R'''' can be the same or different and are independently selected from the group consisting of amino, sulfonate, carboxylate, hydroxamate, phosphonate, and pyridyl groups.

In a further aspect of the invention, the metal ion of the above composition is an element with atomic number Z, which is 12 and/or within the ranges of 20–31, 38–50, and 56–82. In a specific embodiment of the invention, the metal ion is selected from the group consisting of calcium, cadmium, copper, yttrium, and lanthanum. The co-ligand is selected from the group consisting of heterocyclic N-oxides, phenols, anilines, and nitrobenzenes. More specifically, the co-ligand is selected from the group consisting of pyridine N-oxide, quinoline-N-oxide, phenol, aniline, and nitrobenzene.

DETAILED DESCRIPTION OF THE INVENTION p-Sulfonatocalix[4]arene is a macrocyclic anion having a truncated pyramid shape and containing a hydrophobic cavity bounded by four aromatic rings. The base and apical square faces of the truncated pyramid are defined by sulfonate groups and phenolic hydroxyl groups respectively, and the trapezoidal faces consist of the external surfaces of the aromatic rings. As used herein, "up" and "down" orientations of the truncated pyramid refer to the position that would be occupied by the apex of the pyramid if it were not truncated. Since the negatively charged sulfonate groups repel each other electrostatically, they form the base of the pyramid, while the hydroxyl groups are directed toward the apex. The p-sulfonatocalix[4]arene shown below is in the "down" orientation.

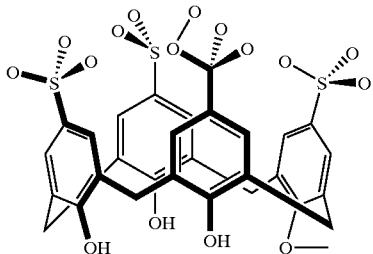

The bipolar amphiphilic nature of p-sulfonatocalix[4] arene, in conjunction with its truncated pyramidal shape, serves as a dominant structure-directing factor in the organization of this macrocycle in its solid-state structures. For example, in the crystal structure of $Na_5$[p-sulfonatocalix[4] arene] (J. L. Atwood, A. W. Coleman, H. Zhang, S. G. Bott, *J. Incl. Phenom.* 5, 203 (1989)), the hydrophobic cores of the truncated pyramids align to form a bilayered structure consisting of alternating organic and aqueous layers. This structure is consistent with the arrangement of a bipolar amphiphilic molecule according to the influences of hydrophobic effects. The aqueous layers are composed of the polar surfaces of the truncated pyramids, water molecules, and counter ions. The organic layers consist of a π-stacked, two-dimensional bilayered grid composed of truncated pyramids arranged in an alternating "up-down," antiparallel fashion with their aromatic rings in van der Waals contact with those of adjacent calixarene molecules. This aspect of the structure may be interpreted in terms of organization of the truncated pyramids according to shape complementarity (G. M. Whitesides, J. P. Mathias, C. T. Seto, *Science* 254, 1312 (1991); A. Terfort, N. Bowden, G. M. Whitesides, *Nature* 386, 162 (1997)).

Although the bilayer arrangement of p-sulfonatocalix[4] arene persists in many of its structures (see J. L. Atwood et al., *J. Am. Chem. Soc.* 113, 2760 (1991); J. L. Atwood et al., *Inorg. Chem.* 31, 603 (1992)), the inventors found that it is possible to influence the relative orientation of the truncated pyramids with respect to each other, and in particular to alter the orientation of the truncated pyramids into an "up-up" arrangement.

Figure 1A:
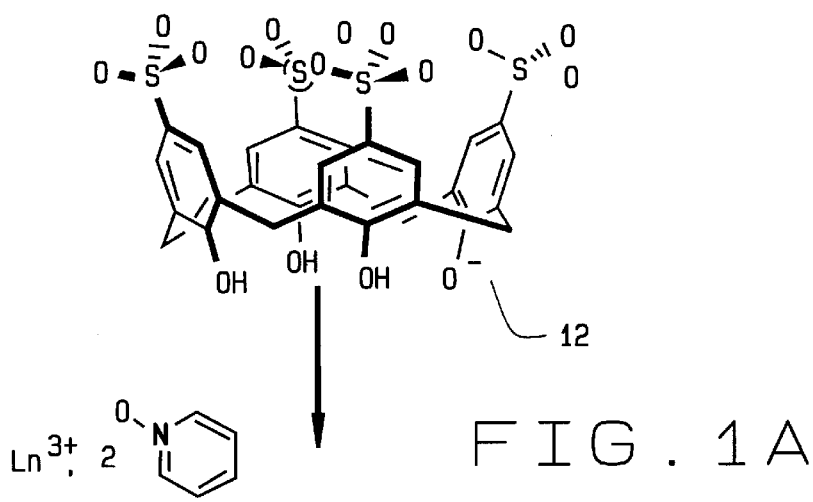
FIGS. 1A, 1B, and 1C schematically depicts the reaction of p-sulfonatocalix[4]arene anions with pyridine N-oxide and La(III) (2:2:1 mole ratio) to form a C-shaped dimeric assembly that forms the basic unit of a spherical assembly.
Figures 1B, 1C:
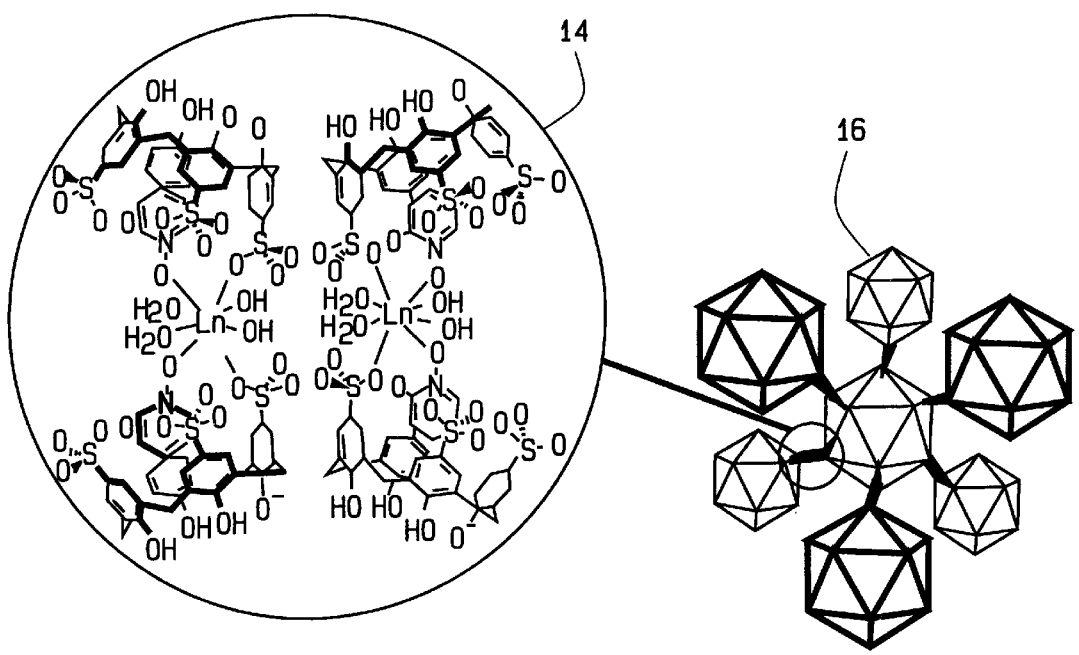

Referring to FIGS. 1A, 1B, and 1C, addition of 2 moles of pyridine N-oxide to an aqueous solution comprising 2 moles of p-sulfonatocalix[4]arene pentaanion 12 and 1 mole of a lanthanide metal ($Ln^{3+}$) nitrate yields a framework in which two p-sulfonatocalix[4]arene anions coordinate to a La(III) ion through their sulfonate groups to form C-shaped dimeric assembly 14. FIG. 1B shows the dimeric assembly 14 which provides linkages between spheres 20 (shown in FIG. 2) which are connected through the linkages 14 (shown in enlarged form in FIG. 1B) to form an assembly 16 of the spheres (as shown in FIG. 1C). In addition, two pyridine N-oxide ligands, both of which coordinate to the La(III) ion, bind within the respective calixarene cavities of the dimer. In these dimeric assemblies, the $Ln^{3+}$ ion acts as a hinge while the steric requirements of the pyridine N-oxide ligands binding concomitantly to the $Ln^{3+}$ ion and the calixarene cavities impart a dihedral angle of 60° between the p-sulfonatocalix[4]arene molecules.

Figure 2:
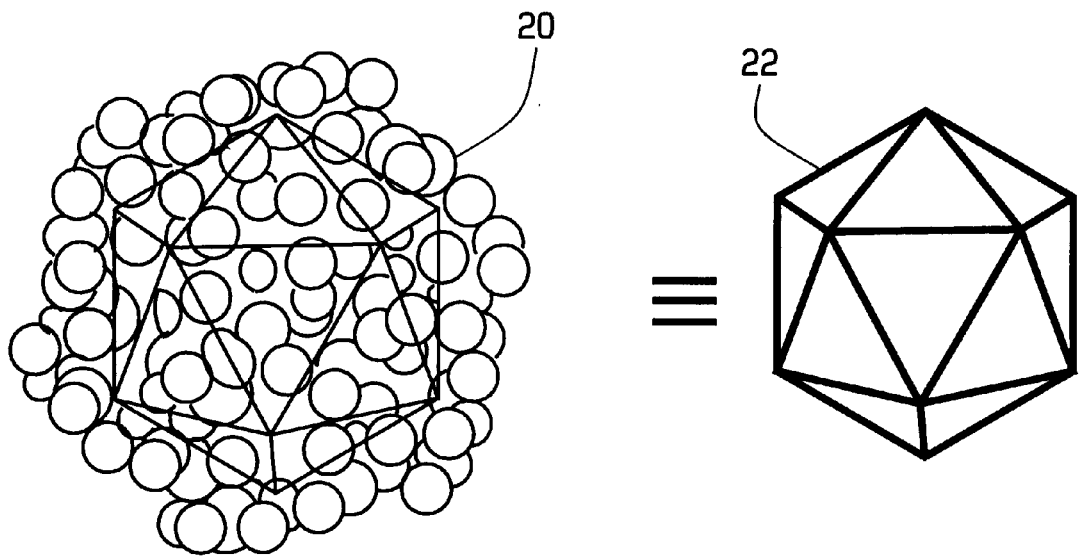
FIG. 2 shows an external and cross-sectional view of a space-filling model of the sphere formed by p-sulfonatocalix [4]arene anions in the presence of pyridine N-oxide and La(III) (2:2:1 mole ratio).
Figure 2:
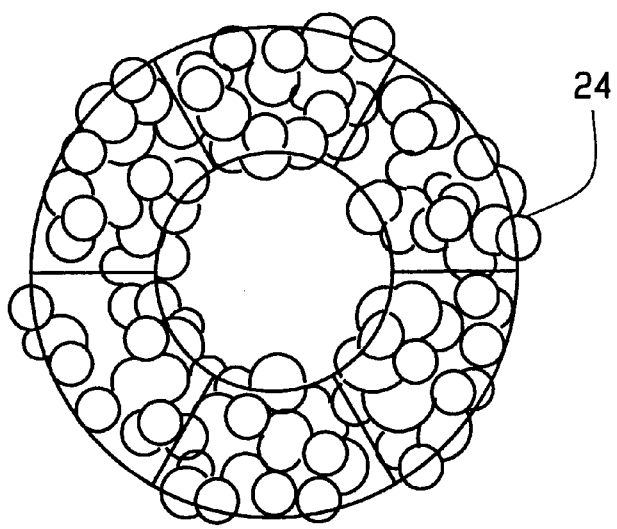

This dihedral angle helps p-sulfonatocalix[4]arene to assemble into structures with curved surfaces, such as spherical clusters composed of 12 p-sulfonatocalix[4]arene pentaanions 12 arranged at the vertices of an icosahedron, to form spherical structure 20 based upon icosahedral structure 22, as shown in FIG. 2. Each spherical structure 20 measures approximately 28 Å (2.8 nm) in diameter and has a volume of approximately 11,000 Å$^3$, depicted in cross-section 24 of spherical structure 20. As in the bilayer structures observed for $Na_5$(p-sulfonatocalix[4]-arene), the hydrophobic regions of the truncated pyramid-shaped anions are aligned, but in this case they are assembled in an "up-up," radially symmetric fashion along the surface of a sphere, where they constitute an organic shell around an aqueous polar core. Thus, 48 negatively charged sulfonate groups from the larger faces of 12 truncated pyramids lie on the exterior of the sphere and define a polar, outer shell surface. Similarly, a polar, inner shell surface comprises 48 phenolic hydroxyl groups, 12 of which are deprotonated, from the smaller faces of the truncated pyramids. This arrangement is consistent with that often observed in unilamellar vesicles in which the larger polar head groups of bipolar amphiphiles are preferentially oriented toward the external surface of the membrane, while the smaller polar headgroups are oriented toward the interior.

The cavities of the calixarenes in spherical structure 20 lie just below the polar surface of the sphere and constitute a series of hydrophobic pockets. Twelve pyridine N-oxide molecules penetrate the polar surface of each sphere and bind within the hydrophobic pockets through π-stacking interactions, while their oxygen atoms extend outward from the pockets and coordinate to La(III) ions above the sphere surface. The aqueous, interstitial areas between spheres contain, in addition to La(III) ions, an intricate H-bonded network of water molecules and hydrated $Na^+$ ions. The core of each spherical structure 20 has a diameter of approximately 15 Å and a volume of approximately 1700 Å$^3$ and contains a well-defined cluster consisting of 30 water molecules and two Na+ ions.

Figure 3:
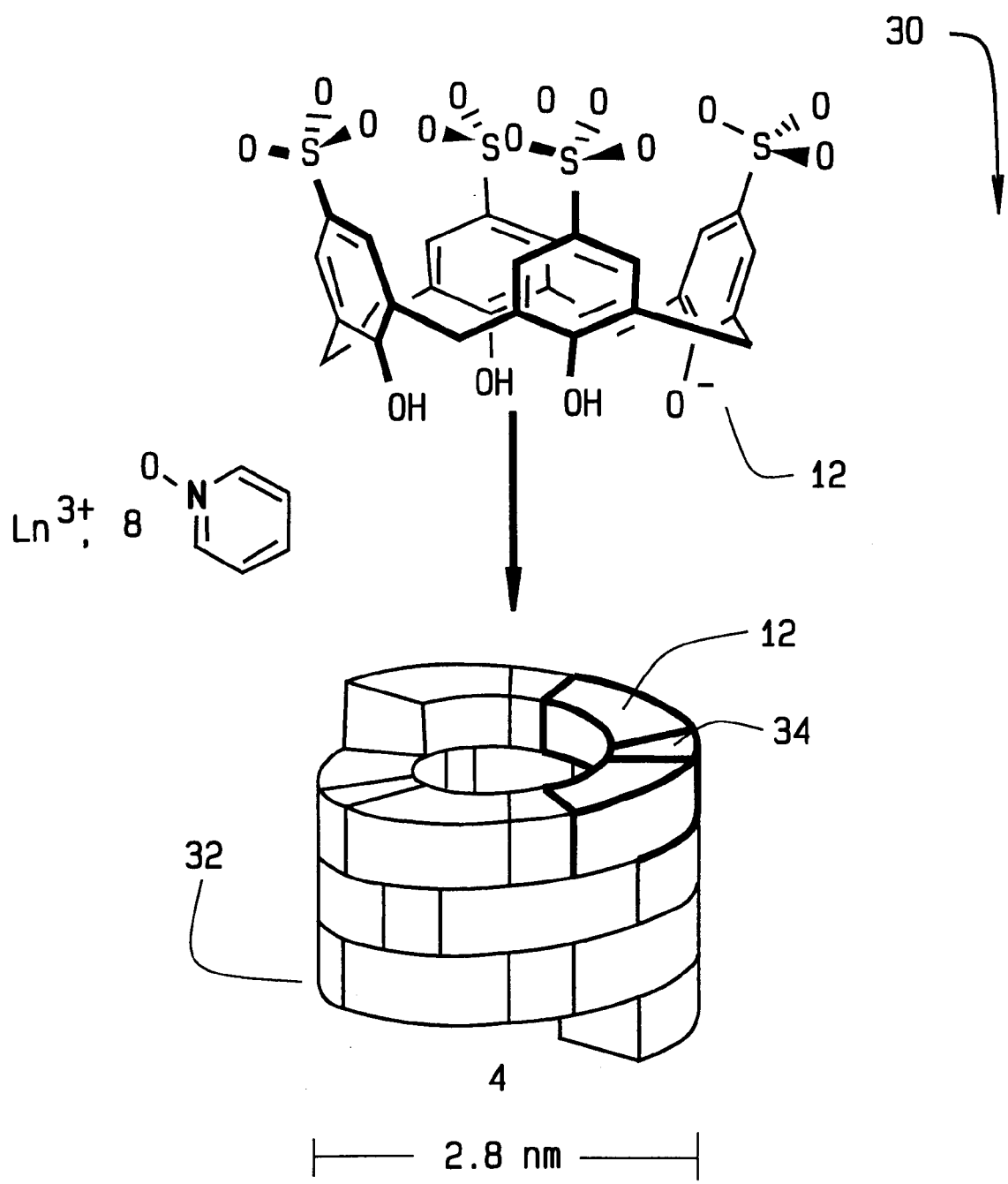
FIG. 3 schematically depicts the self-organization of p-sulfonatocalix[4]arene anions with pyridine N-oxide and La(III) (2:8:1 mole ratio) into structures with tubular morphology.
Figure 4A:
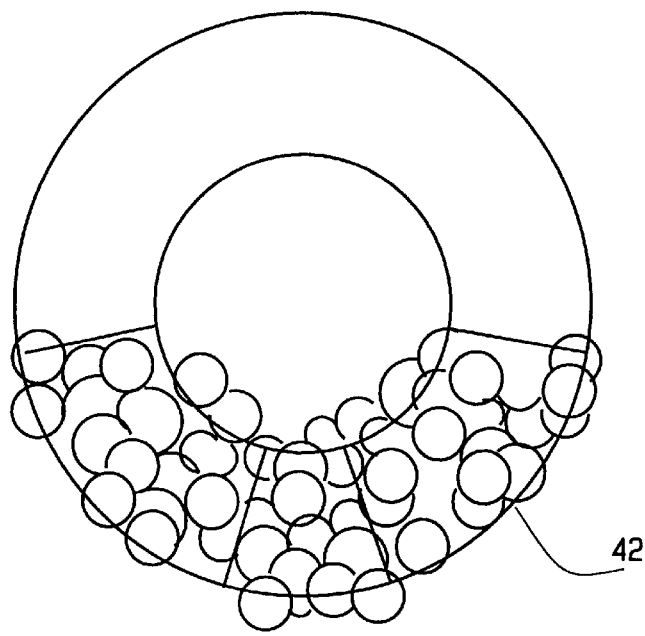
FIG. 4A shows a partial cross-sectional view of the tubular structure showing the arrangement of p-sulfonatocalix[4]arene anions, pyridine N-oxide, and La(III) (outlined) to form the curved surface that defines the tube.
Figure 4B:
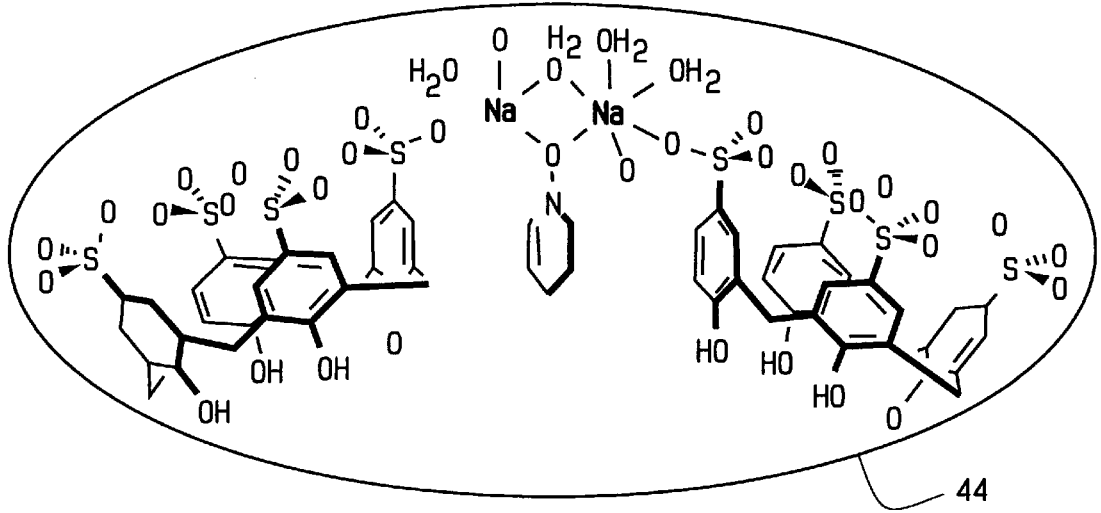
FIG. 4B shows the molecular structure of the repeating unit.

Referring to FIG. 3 and FIG. 4, addition of 8 moles of pyridine N-oxide to an aqueous solution comprising 2 moles of p-sulfonatocalix[4]arene pentaanion 12 and 1 mole of a lanthanide metal ($Ln^{3+}$) nitrate yields crystals of tubular structure 32 after several days. Each tubular structure 32 is approximately 28 Å (2.8 nm) in diameter and consists of p-sulfonatocalix[4]arene molecules 12 arranged along the surface of a cylinder. The tubes are aligned with the long axis of the needle-shaped crystals and therefore have lengths approaching 1 cm in some cases. The tubular structure 32 in cross-section view 42 bears a close resemblance to that of cross-section 24 of spherical structure 20 (shown in FIG. 2) and consists of an analogous polar core, an organic shell, and a polar, inner and outer shell surface. As in spherical structure 20 (shown in FIG. 2), the sulfonate groups of the truncated pyramid-shaped calixarenes comprise a polar outer surface while the hydroxyl groups define a polar, inner shell surface. In tubular structure 32, however, the organic shell is no longer composed purely of calixarene molecules but now contains two crystallographically unique pyridine N-oxide molecules 34 intercalated between the aromatic rings of adjacent calixarenes. One type of pyridine N-oxide 34 is disordered and is oriented such that its oxygen atom is directed toward the interior of the tube. The other type is oriented such that its oxygen atom is directed toward the outer polar surface of the tube where it coordinates to Na+ ions in insert 44. In addition, each pyridine N-oxide molecule participates in π-stacking interactions (both T-shaped and parallel-offset types) with the aromatic rings of four surrounding calixarene molecules.

Another notable feature of tubular structure 32 is that the p-sulfonatocalix[4]arene pentaanion 12 and the intercalated pyridine N-oxide molecules form a chiral, helical assembly along the length of the tube. The helix consists of a single strand of alternating p-sulfonatocalix[4]-arene pentaanions 12 and pyridine N-oxide molecules, and there are 4.5 of these units in each turn. These tubular assemblies are arranged in a hexagonal array in a pattern similar to the organization of cylindrical micelles. The Na+ ions assist in stabilizing the tubular assemblies by coordinating to the sulfonate groups of calixarenes in adjacent turns of the helix. In this structure, there are two types of pyridine N-oxide molecules that fill the calixarene cavities. One type of pyridine N-oxide is bound within the calixarenes of C-shaped dimeric assembly 14, and is coordinated to La(III) ions that, in turn, join adjacent tubes. The second type of pyridine N-oxide is disordered and its oxygen atom extends into a triangular-shaped tunnel lined by the outer surfaces of three adjoining tubes. These tunnels, which contain a disordered network of water molecules and Na+ ions, are created by the hexagonal packing arrangement of the tubes. Here too C-shaped dimeric assemblies 14 persist but the dihedral angle between the calixarene molecules is only about 15°. In proceeding from the sphere to the tube, the aqueous core has become a cylindrical channel with a diameter of 15 Å. This channel, which is not well resolved because of disorder, now contains La(III) ions in addition to the hydrated Na+ ions observed in the spherical core.

The intercalation of pyridine N-oxide into the organic shell has an effect equivalent to increasing the hydrophobic volume of the structural components that make up the shell, but contributing little to their polarity. According to the concept of critical packing parameters, an increase in the volume of the hydrophobic portion of a given amphiphile favors the formation of a cylindrical rather than a spherical structure. This model offers at least a qualitative explanation for the transition from the spherical morphology of spherical structure 20 to the tubular morphology of tubular structure 32.

The generality of this design strategy was explored with respect to a number of factors. Spherical structures analogous to spherical structure 20 are obtained with other lanthanide ions including Pr, Nd, Eu, Gd, Tb, Dy, Er, and Yb. In the case of the tubular structure 32 it was possible to obtain an analogous tubular structure for Gd and Yb. Although there are slight differences in unit cell dimensions and in some minor features of the structures, the spherical and tubular calixarene assemblies are essentially identical throughout the series. Therefore, it appears that variations in the size of the lanthanide ions are absorbed by subtle changes in intermolecular bond distances and angles in the surrounding interstitial areas, but the geometry of the spheres and tubes is conserved.

The instant compounds find use as a way of encapsulating drugs including, but not limited to, the antihistamine fexofenadine hydrochloride ((±)-4-[1-hydroxy-4-[4-(hydroxydiphenyl-methyl)-1-piperidinyl]butyl]-α,α-dimethyl benzeneacetic acid hydrochloride, sold in the US as Allegra™), loratadine (4-(8-chloro-5,6-dihydro-11H-benzo-[5,6]cyclohepta[1,2-b]pyridin-11-ylidene)-1-piperidinecarboxylic acid ethyl ester, sold in the US as Claritin™), buproprin 1-(3-chlorophenyl)-2-[(1,1-dimethylethyl)amino]-1-propanone hydrochloride, sold in the US as Wellbutrin™, divalproex sodium, a compound of sodium valproate (sodium 2-propylpentanoate) and the parent acid, sold in the US as Depakote™, and gabapentin (1-[aminomethyl]-cyclohexane-acetic acid, sold in the U.S. as Neurontin™).

This work has been described in detail (Orr, G. W.; Barbour, L. J.; Atwood, J. L.; *Science* vol. 285, p. 1049–1052 (1999)), the disclosure of which is incorporated by reference in its entirety.

EXAMPLE 1

Aqueous solutions of $Na_5$(p-sulfonatocalix[4]arene) (0.283 M), pyridine N-oxide (3.07 M), and $La(NO_3)_3.6H_2O$ (1.15 M) were combined in a 2:2:1 molar ratio. After about 1 hour, crystals formed that were suitable for single-crystal X-ray diffraction analysis. The spherical assembly crystallizes in the trigonal system, space group R3 (no.148), a=b=44.553(4) Å, c=35.223(4) Å, V=60549(10) Å$^3$, z=18, $\rho_{calc}$=1.300 g cm$^{-3}$, λ(Mo Kα)=0.70930 A. The crystal structure reveals a framework in which two p-sulfonatocalix[4]arene anions coordinate to a La(III) ion through their sulfonate groups to form a C-shaped dimeric assembly, as shown in FIG. 1B. In addition, two pyridine N-oxide ligands, both of which coordinate to the La(III) ion, are bound within the respective calixarene cavities of the dimer. In these dimeric assemblies, the $Ln^{3+}$ ion acts as a hinge while the steric requirements of the pyridine N-oxide ligands binding concomitantly to the $Ln^{3+}$ ion and the calixarene cavities, imparts a dihedral angle of 60° between the p-sulfonatocalix[4]arene molecules.

EXAMPLE 2

Aqueous solutions of $Na_5$(p-sulfonatocalix[4]arene) (0.283 M), pyridine-N-oxide (3.07 M), and $La(NO_3)_3.6H_2O$ (1.15 M) were combined in a 2:8:1 molar ratio and deposited needle-shaped crystals after approximately one hour. The tubular assembly crystallizes in the trigonal system, space group P3$_1$12 (no.151), a=b=30.4533(11) Å, c=16.2800(8) Å, V=13075.4(9) Å$^3$, z=3, $\rho_{calc}$=1.733 g cm$^3$, λ (Mo Kα)= 0.70930 A. Crystallographic analysis of these crystals revealed a tubular assembly (4), approximately 28 Å (2.8 nm) in diameter and consisting of p-sulfonatocalix[4]arene molecules arranged along the surface of a cylinder. The tubes were aligned with the long axis of the needle-shaped crystals and have lengths approaching I cm in some cases.

EXAMPLE 3

Aqueous solutions of $Na_5$(p-sulfonatocalix[4]arene) (0.283 M), pyridine N-oxide (3.07 M), and $Cd(NO_3)_2$ (1.20 M) were combined in a 2:2:1 molar ratio. After about 1 hour, crystals formed that were suitable for single-crystal X-ray diffraction analysis. The spherical assembly crystallizes in the trigonal system, space group R3 (no.148), a=b=45.082 (2) Å, c=30.814(2) Å, z=18. The crystal structure was not refined, but a spherical structure could be seen in the preliminary x-ray structure.

EXAMPLE 4

Aqueous solutions of $Na_5$(p-sulfonatocalix[4]arene) (0.283 M), pyridine N-oxide (3.07 M), and $Cd(NO_3)_2$ (1.20 M) were combined in a 1:1:1 molar ratio. After about 1 hour, crystals formed that were suitable for single-crystal X-ray diffraction analysis. The spherical assembly crystallizes in the trigonal system, space group R3 (no.148), a=b=45.082 (2) Å, c=30.814(2) A, z=18.

EXAMPLE 5

Aqueous solutions of $Na_5$(p-sulfonatocalix[4]arene) (0.283 M), pyridine N-oxide (3.07 M), and $Ca(NO_3)_2$ (1.05

M) are combined in a 2:2:1 molar ratio. An aqueous solution of gabapentin (1.00 M) is added to the 2:2:1 aqueous solution such that the ratio of components is 2:2:1:0.167, where the 0.167 is the gabapentin. The spherical assembly is then crystallized with the gabapentin encapsulated in the sphere. The drug-containing compound is characterized by X-ray diffraction, solid state NMR, IR, and electrospray mass spectrometry. The encapsulated gabapentin is administered as an oral formulation that has improved sustained release properties.

EXAMPLE 6

Aqueous solutions of $Na_5$(p-sulfonatocalix[4]arene) (0.283 M), pyridine N-oxide (3.07 M), and $Ca(NO_3)_2$ (1.05 M) are combined in a 2:8:1 molar ratio. An aqueous solution of gabapentin (1.00 M) is added to the 2:8:1 aqueous solution such that the ratio of components is 2:8:1:0.167, where the 0.167 is the gabapentin. The mixture is then crystallized with the gabapentin encapsulated in the tubule structure. The drug-containing compound is characterized by X-ray diffraction, solid state NMR, IR, and electrospray mass spectrometry.

EXAMPLE 7

Aqueous solutions of $Na_5$(p-sulfonatocalix[4]arene) (0.283 M), pyridine N-oxide (3.07 M), and $Ca(NO_3)_2$ (1.05 M) are combined in a 2:2:1 molar ratio. An aqueous solution of fexofenadine hydrochloride (1.00 M) is added to the 2:2:1 aqueous solution such that the ratio of components is 2:2:1:0.167, where the 0.167 is the fexofenadine hydrochloride. The spherical assembly is then crystallized with the fexofenadine encapsulated in the sphere. The drug-containing compound is characterized by X-ray diffraction, solid state NMR, IR, and electrospray mass spectrometry.

EXAMPLE 8

Aqueous solutions of $Na_5$(p-sulfonatocalix[4]arene) (0.283 M), pyridine N-oxide (3.07 M), and $Ca(NO_3)_2$ (1.05 M) are combined in a 2:8:1 molar ratio. An aqueous solution of fexofenadine hydrochloride (1.00 M) is added to the 2:8:1 aqueous solution such that the ratio of components is 2:8:1:0.167, where the 0.167 is the fexofenadine hydrochloride. The mixture is then crystallized with the fexofenadine contained in the tubule structure. The drug-containing compound is characterized by X-ray diffraction, solid state NMR, IR, and electrospray mass spectrometry.

EXAMPLE 9

Aqueous solutions of $Na_5$(p-sulfonatocalix[4]arene) (0.283 M), pyridine N-oxide (3.07 M), and $Y(NO_3)_3.6H_2O$ (1.15 M) are combined in a 2:8:1 molar ratio. An aqueous solution of $Ba(NO_3)_2$ and $Cu(NO_3)_2$ in a 2:3 mole ratio (2.10 M and 3.15 M, respectively) is added to the 2:8:1 molar ratio solution such that the ratio of components is 2:8:1:2:3. The mixture is then crystallized with the Y, Ba, and Cu contained in the tubule structure. The compound is characterized by X-ray diffraction, solid state NMR, IR, and electrospray mass spectrometry.

EXAMPLE 10

Aqueous solutions of $Na_5$(p-sulfonatocalix[4]arene) (0.283 M), 2 (3.07 M), and $Ca(NO_3)_2$ (1.05 M) are combined in a 2:2:1 molar ratio. A solution of sodium valproate in acetone (1.00 M) is added to the 2:2:1 aqueous solution such that the ratio of components is 2:2:1:0.167, where the 0.167 is the sodium valproate. The spherical assembly is then crystallized with the sodium valproate encapsulated in the sphere. The drug-containing compound is characterized by X-ray diffraction, solid state NMR, IR, and electrospray mass spectrometry. The encapsulated sodium valproate is administered in an oral formulation. The drug-containing compound has improved handling properties because it is less hygroscopic and it has improved sustained release properties.

While the invention has been described in terms of various specific embodiments, those skilled in the art will recognize that the invention can be practiced with modification within the spirit and scope of the claims.

What is claimed is:

1. A composition comprising a calixarene, a co-ligand, and a 2+ or 3+ metal ion in a ratio of about 1:1:1 to about 2:8:1.

2. The composition of claim 1 wherein the calixarene has the structure

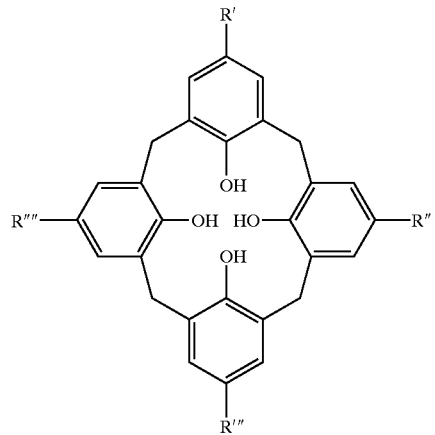

wherein R', R", R'", and R"" are functional groups capable of binding to a metal ion.

3. The composition of claim 2 wherein R', R", R'", and R"" are the same or different and are independently selected from the group consisting of amino, sulfonate, carboxylate, hydroxamate, phosphonate, and pyridyl.

4. The composition of claim 3 wherein R', R", R'", and R"" are sulfonate.

5. The composition of claim 1 wherein the metal ion is an element with atomic number Z=12, 20–31, 38–50, and 56–82.

6. The composition of claim 5 wherein the metal ion is selected from the group consisting of calcium, cadmium, copper, yttrium, and lanthanum.

7. The composition of claim 6 wherein the metal ion is lanthanum.

8. The composition of claim 1 wherein the co-ligand is selected from the group consisting of heterocyclic N-oxides, phenols, anilines, and nitrobenzenes.

9. The composition of claim 1 wherein the co-ligand is selected from the group consisting of pyridine N-oxide, quinoline-N-oxide, phenol, aniline, and nitrobenzene.

10. The composition of claim 1 wherein the composition has a substantially spherical structure.

11. The composition of claim 1 wherein the composition has a substantially tubular structure.

12. The composition of claim 1, further comprising a drug substance.

13. The composition of claim 10, wherein the drug substance is selected from the group consisting of fexofenadine, loratadine, buproprin, sodium valproate, and gabapentin.

14. The composition of claim 1 wherein the calixarene, the co-ligand, and the 2+ or 3+ metal ion are in a ratio of about 2:2:1 to about 2:8:1.

15. A method of controlling topology in a metal complex of a calixarene, comprising the step of adding a co-ligand to a calixarene and a 2+ or 3+ metal ion.

16. The method of claim 15 wherein the co-ligand is selected from the group consisting of heterocyclic N-oxides, phenols, anilines, and nitrobenzenes.

17. The method of claim 16 wherein the co-ligand is selected from the group consisting of pyridine N-oxide, quinoline-N-oxide, phenol, aniline, and nitrobenzene.

18. The method of claim 17 wherein the co-ligand is pyridine N-oxide.

19. The method of claim 15 wherein the calixarene is calix[4]arene.

20. The method of claim 19 wherein the calix[4]arene is p-sulfonatocalix[4]arene.

21. The method of claim 15 wherein the metal ion is an element with atomic number Z=12, 20–31, 38–50, and 56–82.

22. The method of claim 15 wherein the metal complex assembles into a substantially spherical structure.

23. The method of claim 15 wherein the metal complex assembles into a substantially tubular structure.

* * * * *